Dec. 28, 1948. C. H. HAMBURG Plant Pat. 816

AVOCADO TREE

Filed Oct. 26, 1946

CHARLES H. HAMBURG
INVENTOR.

BY C. P. Lee
ATTORNEY.

Patented Dec. 28, 1948

Plant Pat. 816

UNITED STATES PATENT OFFICE

816

AVOCADO TREE

Charles H. Hamburg, Whittier, Calif.

Application October 26, 1946, Serial No. 705,960

1 Claim. (Cl. 47—62)

This invention relates to a new and distinct variety of avocado tree having certain highly desirable characteristics as will appear hereinafter.

One of the most popular and extensively cultivated varieties of avocado is the Fuerte, but this variety has a very irregular spreading habit of growth and reaches maximum production of fruit during February to April, some fruit being available in certain localities as early as the first part of January and the Fuerte season as a whole encompassing December to May. For many years growers have desired a variety of avocado which would bear fruit similar to that of the Fuerte but which would bear fruit during the summer months. The variety known as Lyon bears fruit later than the Fuerte but the fruit of this variety is very much larger; the fruit has a tendency to crack and has an excessively large seed. From a commercial standpoint, excessively large fruit is undesirable because the average housewife cannot dispose of such excessively large avocado at a single meal.

The tree of my new variety originated as a chance seedling from a Guatemalan seedling tree.

The new variety of avocado to which this invention is directed is a tree characterized by an upright, relatively slender, vigorous habit of growth of the central leader type. The branches emanate from the trunk in equally spaced relation and in a slightly upward direction, the outer portions of the branches being substantially horizontal except when heavily loaded with fruit. When heavily loaded with fruit, the outer portions of the branches may droop while the terminals of the branches curl upwardly.

Figure 1:
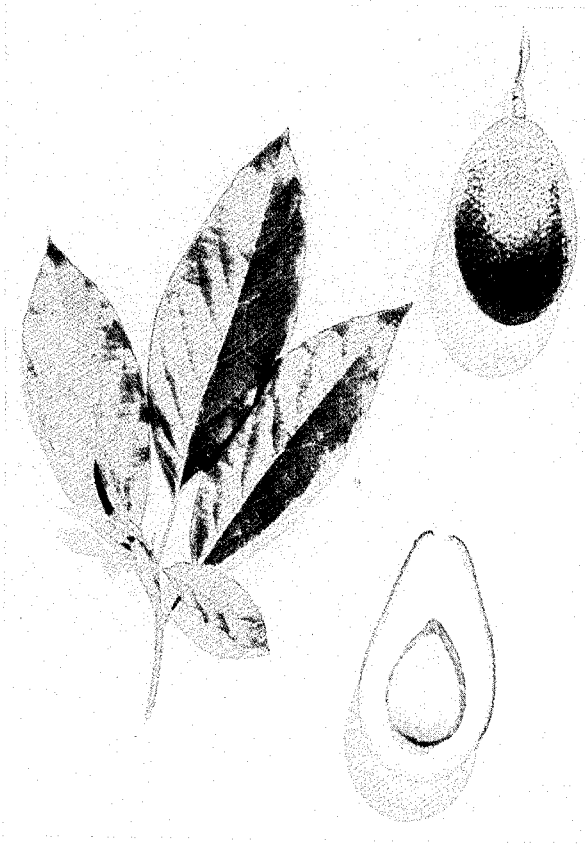
Figure 2:
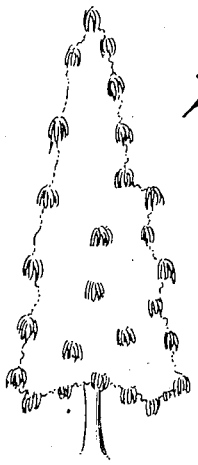
Figure 3:
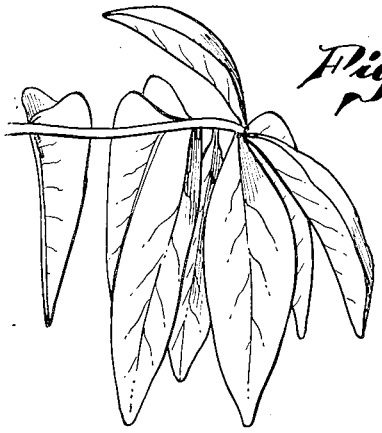

The color plate of the attached sheet of drawings, Fig. 1, illustrates foliage at a terminal branch, the outer appearance of the fruit, and a section through the fruit showing the general contours and relative seed size, with the seed dislodged somewhat to display the covering. Fig. 2 is a sketch illustrating the upright habit of growth of the tree. Fig. 3 illustrates a terminal cluster of the foliage.

The foliage grows in close relationship at the terminals of the branches forming clusters, the mature leaves hanging downwardly in a partly curled or half-closed position so as to produce a distinctive appearance. Young foliage is Cress Green in color (Color Standards and Nomenclature, Ridgway). Mature foliage has its top surface of Dark Cress Green (Plate XXXI—29″—*m*). The back of the leaves ranges from Sage Green to Artemisia Green. The top surface of the leaves is provided with a very fine surface network of wrinkles or indentations, detracting somewhat from the glossy character of the leaves and producing a smooth matted appearance. All foliage is provided with pronounced veins on the rear surface. Young foliage is lanceolate and substantially flat. Mature foliage is lanceolate and in most instances curls into a semicircular section and is provided with a ruffled edge.

The foliage carried by the tree is heavy at all periods, defoliation being gradual during the summer months but not excessive. This characteristic, together with the clusters of foliage at the branch terminals, protects the fruit which is ordinarily found immediately under the heavy clusters of terminal leaves. Moreover, the gradual defoliation protects the branches and trunk so that the tree is not liable to sunburn.

Bloom is heavy but not as prolific as in the Fuerte. The bloom is both terminal and axillary, with a greater proportion of the bloom in the latter relationship. Bud wood is profuse and appears to evidence two bud scales. Propagation is relatively easy. Young branches carry pronounced lenticels of an irregular, oval shape and of a darker green than the branch itself. The lenticels are non-uniformly distributed. Propagation with Ganter root stock has been particularly effective and young trees may bear at the age of two years, particularly when they have been grafted on healthy, large root stock. In one instance, a three-year tree grew to a height of fifteen feet.

The fruit matures during June and July in Southern California, whereas the Fuerte is at its peak during the months of March and April. The fruit is pear shaped and green in general coloration and is provided with a neck which is not excessively long.

The outer skin of the fruit is slightly smoother than that of the Fuerte and appears to be more glossy. The skin is thinner than that of the Lyon and smoother and darker than that of the Lyon. The green background coloration of the outer skin of the fruit ranges from Varleys Green to Hays Green. The spots on the fruit range from Calliste Green to Dull Green-Yellow. Spotting on the surface of the fruit is more concentrated in the lower portions than in the upper portions. The spots appear to be free of the brown heads which are often found on other fruit. The stem and button end is non-axial, being slightly displaced to one side. A dimple appears near the bottom of the fruit opposite the button end. The stem is slightly longer than that of the Fuerte and the button is shallow.

The seed is pointed, medium to large in size, tight within its cavity and provided with a light brown covering. The seed has two lobes and appears to be positioned slightly lower in the fruit than in the Fuerte.

The flesh is firm, not mushy, substantially free from fiber, has a nutty flavor and a high oil content, the oil content generally exceeding 18%. The meat ranges in color from Naphthalene Yellow, Primrose Pale Chalcedony Yellow to Sulphur Yellow, with greater green content near the skin.

The fruit has the ability to hang on the tree even though it is not picked for several months after it becomes mature. In this manner the supply of fruit to the market may be spread over a considerable period of time when the Fuerte is not available. The average fruit weighs from 8 to 10 ounces and the tree appears to have the property of bearing with great regularity and produces a heavy crop each year. The tree has been propagated in the Whittier-La Habra district in Southern California.

The distinguishing characteristics of the tree of this invention appear to be the central leader type, upright habit, the clusters of foliage at the terminals of the substantially horizontal branches, and its ability to bear relatively thin-skinned, green fruit during June and July. It is to be understood that departures from the specific description given may occur due to climatic conditions, soil, etc.

I claim:

A variety of avocado tree substantially as disclosed, characterized by an upright, central leader type, slender and vigorous habit, uniformly distributed branches, and clusters of foliage at terminals of the branches, said tree bearing a relatively thin-skinned, green fruit maturing in greatest proportion during June and July when propagated in Southern California.

CHARLES H. HAMBURG.

REFERENCES CITED

The following references are of record in the file of this patent:

UNITED STATES PATENTS

| Number | Name | Date |
|---|---|---|
| P. Pt. 139 | Hass | Aug. 27, 1935 |

OTHER REFERENCES

California Avocado Assn. Yearbook for 1931, page 16.